United States Patent
Doyle

(10) Patent No.: US 10,695,434 B2
(45) Date of Patent: Jun. 30, 2020

(54) PREVENTING CENTRAL NERVOUS SYSTEM INDUCED NAUSEA THROUGH USE OF VITAMIN $B_{12}$ CONJUGATION

(71) Applicant: Robert P. Doyle, Manlius, NY (US)

(72) Inventor: Robert P. Doyle, Manlius, NY (US)

(73) Assignee: Syracuse University, Syracuse, NY (US)

( * ) Notice: Subject to any disclaimer, the term of this patent is extended or adjusted under 35 U.S.C. 154(b) by 0 days.

(21) Appl. No.: 16/267,883

(22) Filed: Feb. 5, 2019

(65) Prior Publication Data

US 2019/0240341 A1    Aug. 8, 2019

Related U.S. Application Data

(60) Provisional application No. 62/626,456, filed on Feb. 5, 2018.

(51) Int. Cl.
| | |
|---|---|
| *A61K 47/55* | (2017.01) |
| *A61K 38/17* | (2006.01) |
| *A61K 31/714* | (2006.01) |
| *A61K 38/26* | (2006.01) |
| *A61K 49/00* | (2006.01) |

(52) U.S. Cl.
CPC .......... *A61K 47/551* (2017.08); *A61K 31/714* (2013.01); *A61K 38/1703* (2013.01); *A61K 38/26* (2013.01); *A61K 49/0032* (2013.01); *A61K 49/0052* (2013.01)

(58) Field of Classification Search
CPC . A61K 31/714; A61K 38/1703; A61K 47/551
See application file for complete search history.

(56) References Cited

U.S. PATENT DOCUMENTS 8,039,432 B2 * 10/2011 Bridon ................. A61K 47/643
514/15.2

FOREIGN PATENT DOCUMENTS

WO    WO-2017181007 A1 * 10/2017 ............. A61K 47/64

OTHER PUBLICATIONS

Bonaccorso et. al. (Molecular pharmaceutics, 2015, 12, 3502-3506) i (Year: 2015).*

* cited by examiner

*Primary Examiner* — Savitha M Rao
(74) *Attorney, Agent, or Firm* — Bond Schoeneck & King, PLLC; David Nocilly; George McGuire

(57) ABSTRACT

A method for the avoidance of side effects associated with glucagon-like peptide-1 receptor (GLP-1R) agonists through vitamin $B_{12}$ conjugation prior to administration. Vitamin $B_{12}$ may be bound to a GLP-1R agonist, such as exendin-4 (Ex4), to provide enhanced proteolytic stability while retaining GLP-1R agonism. The conjugate ($B_{12}$-Ex4) also improves glucose tolerance without producing anorexia and malaise. A GLP-1R agonist that is resistant to DPP-IV degradation and does not penetrate readily into the CNS, but retains the enhanced pharmacokinetic and pharmacodynamic profile on pancreatic β-cells provide a pharmacological tool for glycemic control in type 2 diabetes mellitus (T2DM) patients without eliciting unwanted hypophagia and nausea.

9 Claims, 8 Drawing Sheets

Figure 1:
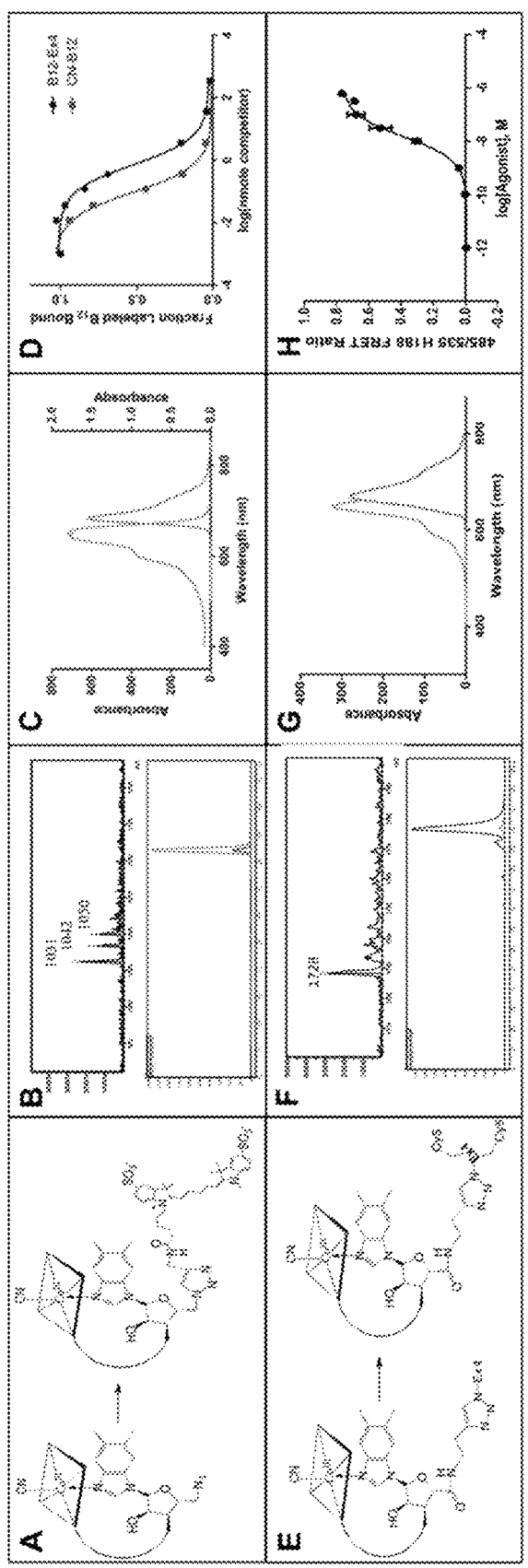

PREVENTING CENTRAL NERVOUS SYSTEM INDUCED NAUSEA THROUGH USE OF VITAMIN $B_{12}$ CONJUGATION

CROSS-REFERENCE TO RELATED APPLICATIONS

The present application claims priority to U.S. Provisional App. No. 62/626,456 filed on Feb. 5, 2018.

BACKGROUND OF THE INVENTION

1. Field of the Invention

The present invention relates to the avoidance of central nervous system side effects and, more particularly, to the use of $B_{12}$ conjugation to prevent.

2. Description of the Related Art

Multiple incretin-based therapeutics are approved for the treatment of type 2 diabetes mellitus (T2DM) due to their ability to elicit pancreatic insulin secretion and reduce blood glucose levels. These pharmacotherapies include compounds designed to increase endogenous concentrations of the incretin hormone glucagon-like peptide-1 (GLP-1) by inhibiting the endopeptidase DPP-IV, as well as synthetic peptide-based GLP-1 receptor (GLP-1R) agonists resistant to DPP-IV degradation. In addition to being the more potent class of GLP-1-based therapeutics for reducing glycemia, GLP-1R agonists significantly reduce food intake and body weight in both humans and animal models. This anorectic effect is attractive when considering the utilization of GLP-1R agonists as an on- or off-label treatment option for obesity, and indeed, the GLP-1R agonist liraglutide is FDA-approved for the treatment of obesity. However, a sizeable percentage of individuals with T2DM do not have obesity or overweight and may want to avoid weight loss. Furthermore, it is important to note that the hypophagic effects of all GLP-1R agonists on the market are accompanied by pronounced incidence of nausea, vomiting, and malaise. In fact, ~20-50% of T2DM patients prescribed GLP-1-based medication experience nausea and/or vomiting, leading to discontinuation of drug treatment in ~6-10% and reduced dose tolerance in another ~15%. These adverse effects are surprisingly under-investigated, as they limit the widespread use, efficacy, and potential ubiquitous utility of GLP-1R agonists (e.g. liraglutide, exenatide) for the treatment of metabolic disease.

Thus, while pharmacological glucagon-like peptide-1 receptor (GLP-1R) agonists may be FDA-approved for treating type 2 diabetes mellitus (T2DM) and obesity, the major side effects such as nausea/malaise reduce the overall market and effectiveness of treatment. Accordingly, there is a need in the art for an approach that avoids the side effects associated with glucagon-like peptide-1 receptor (GLP-1R) agonists while maintaining the efficacy of the agonist.

BRIEF SUMMARY OF THE INVENTION

The present invention comprises the avoidance of side effects associated with glucagon-like peptide-1 receptor (GLP-1R) agonists through vitamin $B_{12}$ conjugation prior to administration. More specifically, vitamin $B_{12}$ may be bound to, for example, the GLP-1R agonist exendin-4 (Ex4), which displays enhanced proteolytic stability and retention of GLP-1R agonism. The conjugate ($B_{12}$-Ex4) was found to improve glucose tolerance without producing anorexia and malaise. A novel GLP-1R agonist that is resistant to DPP-IV degradation, does not penetrate readily into the CNS, but retains the enhanced pharmacokinetic and pharmacodynamic profile of such agonists on pancreatic β-cells would provide a new, improved pharmacological tool for glycemic control in type 2 diabetes mellitus (T2DM) patients without eliciting unwanted hypophagia and nausea.

The effects of systemic $B_{12}$-Ex4 and unconjugated Ex4 on food intake and body weight change, oral glucose tolerance, and nausea/malaise in male rats, and on intraperitoneal glucose tolerance in mice was evaluated. To evaluate whether differences in the profile of effects of $B_{12}$-Ex4 versus unconjugated Ex4 are due to altered CNS penetrance, rats received systemic injections of fluorescein-Ex4 (Flex), Cy5-$B_{12}$ or Cy5-$B_{12}$-Ex4 and brain penetrance was evaluated using confocal microscopy. Uptake of systemically administered Cy5-$B_{12}$-Ex4 in insulin-containing pancreatic beta cells was also examined.

It was found that $B_{12}$-Ex4 conjugate improves glucose tolerance, but does not elicit the malaise and anorexia produced by unconjugated Ex4. While Flex robustly penetrates into the brain (dorsal vagal complex, paraventricular hypothalamus), Cy5-$B_{12}$ and Cy5-$B_{12}$-Ex4 fluorescence were not observed centrally, supporting a lack of CNS penetrance in line with the observed reduction in CNS-associated Ex4 side effects. Cy5-$B_{12}$-Ex4 colocalizes with insulin in the pancreas, suggesting direct pancreatic action as a potential mechanism underlying the hypoglycemic effects of $B_{12}$-Ex4.

These findings highlight the clinical utility of $B_{12}$-Ex4 conjugates as possible future T2DM therapeutics with reduced incidence of adverse effects. Vitamin $B_{12}$ analogs, including but not limited to, cobinamides are viable for the approach of the present invention.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 1 is a series of graphs of (A) Synthetic scheme for Cy5-$B_{12}$, Cy5 alkyne was "clicked" onto a $B_{12}$-azide conjugate. (B) RP-HPLC of Cy5-$B_{12}$ showing purity ≥98% and LC-MS showing 1031[M+2H]$^{+2}$, 1042[M+Na+2H]$^{+2}$, and 1050 [M+K+2H]$^{+2}$, consistent with the conjugate. (C) Excitation and emission spectra of Cy5-$B_{12}$ at 645 and 682 nm, respectively. (D) Human recombinant TCII binding of $B_{12}$-Ex4 and cyano-$B_{12}$ with a $K_d$ of 0.75 and 0.98 nM, respectively. (E) Synthetic scheme for Cy5-$B_{12}$-Ex4, Cy5-NHS ester was conjugated to Ex4's lysine 26 and N-terminal. (F) RP-HPLC of Cy5-$B_{12}$-Ex4 showing purity ≥91% and LC-MS showing m/z=1728 [M+4H]$^{+4}$, consistent with conjugate containing two molecules of Cy5 per $B_{12}$-Ex4 component. (G) Excitation and emission spectra of Cy5-$B_{12}$-Ex4 at 648 and 670 nm, respectively. (H) Cy5-$B_{12}$-Ex4 agonism at the GLP-1 receptor reported using the FRET reporter H188; $EC_{50}$=13 nM. Note that $B_{12}$-Ex4 agonism at the GLP-1 receptor was previously reported (68 pM).

Figure 2:
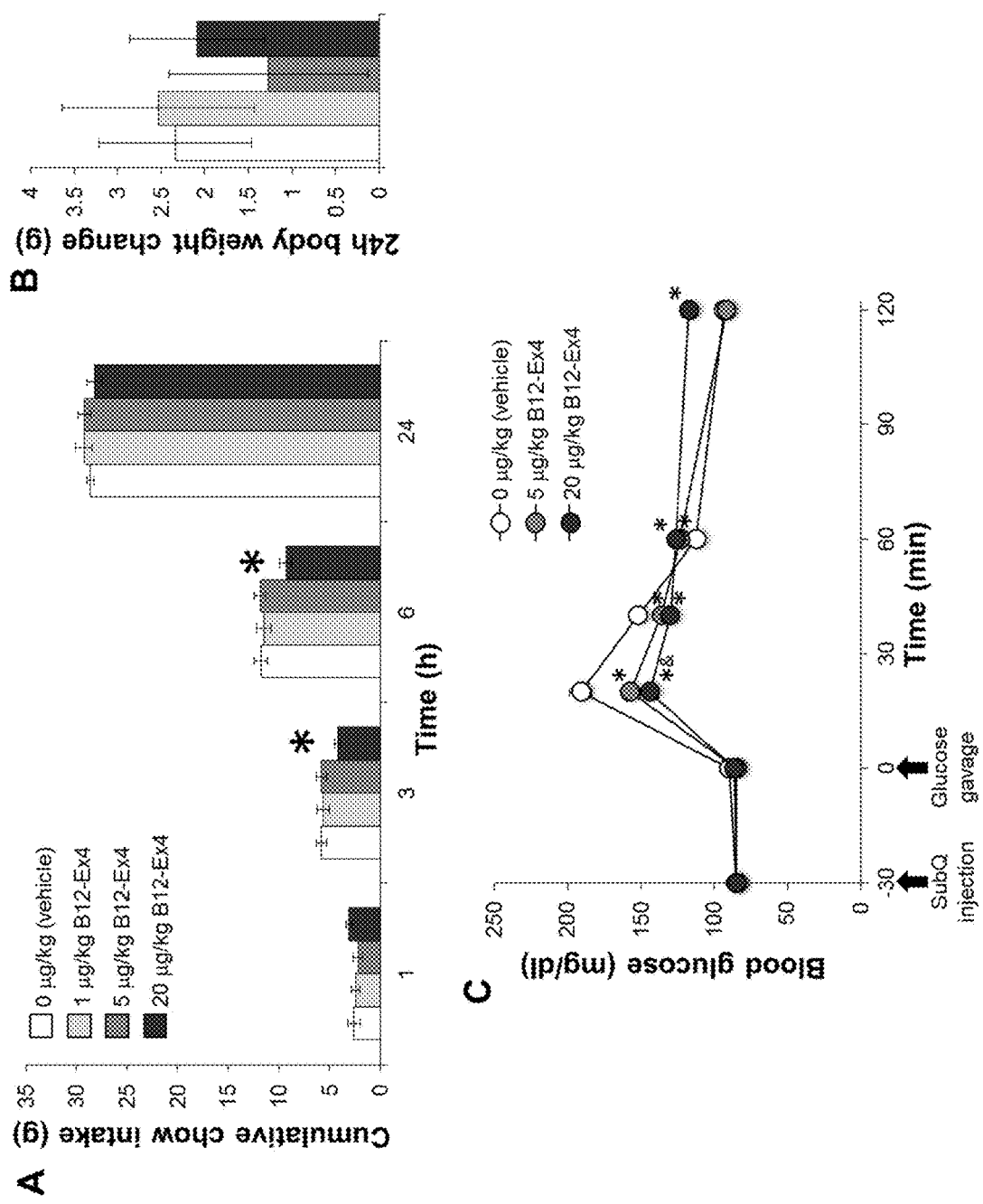

FIG. 2 is a series of graphs showing that $B_{12}$-Ex4 potently suppresses blood glucose in an oral glucose tolerance test but has minimal effects on energy balance control. Food intake and body weight change were measured after SC administration of $B_{12}$-Ex4. Only the highest dose of drug, 20 μg/kg, produced any reduction in feeding (A). No changes in 24 h body weight gain were observed as a result of $B_{12}$-Ex4 administration (B). In a separate experiment, SC injection of $B_{12}$-Ex4 (0 μg/kg indicated by white circles, 5 μg/kg by lighter blue circles, 20 μg/kg by darker blue circles) reduced blood glucose in an oral glucose tolerance test from 20-40 min after injection (C). *, significantly different from vehicle (p<0.05); &, significantly different from 5 μg/kg (p<0.05). Key in (A) also applies to (B). Data are mean±SEM.

Figure 3:
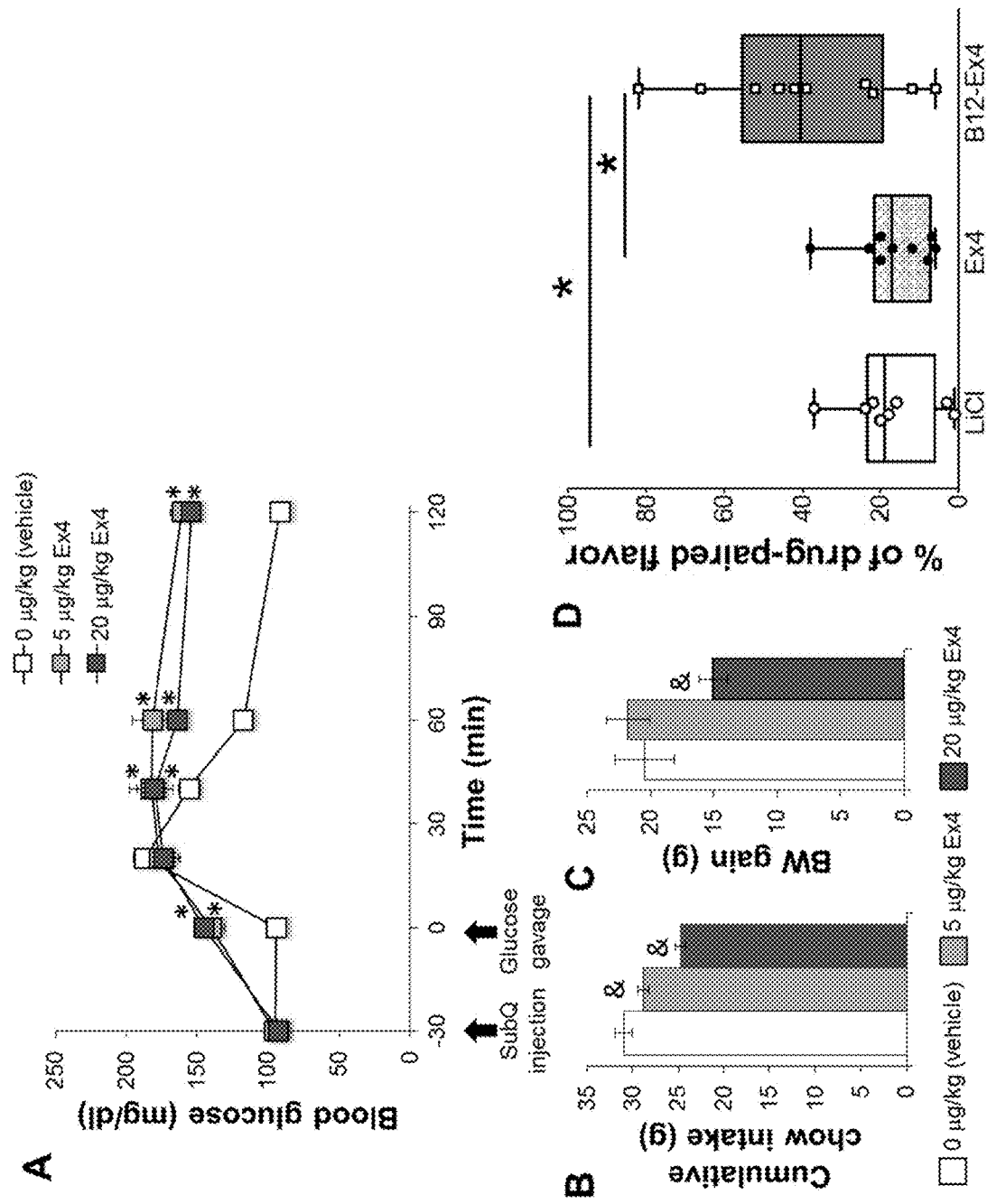

FIG. 3 a series of graphs showing that systemic administration of Ex4 produces a different profile of metabolic effects than $B_{12}$-Ex4. In contrast to the potent suppression of blood glucose produced by $B_{12}$-Ex4, SC injection of Ex4 (0 μg/kg indicated by white squares, 5 μg/kg by lighter red squares, 20 μg/kg by darker red squares) produced a robust hyperglycemic response (A). Food intake (B) and body weight gain (C) were suppressed by SC Ex4. To compare the induction of nausea/malaise by Ex4 with that potentially produced by $B_{12}$-Ex4, rats were tested for expression of a conditioned taste avoidance (CTA) of a flavor paired with IP injection of $B_{12}$-Ex4 (5 μg/kg), Ex4 (5 μg/kg), or LiCl as a positive control (0.15M). The percent acceptance of the drug-paired flavor is shown as a box-and-whiskers plot in (D). Both Ex4 (individual responses represented by black circles, overall group response represented in light gray box) and LiCl (individual responses represented by white circles, overall group response represented in white box) produce avoidance of the drug-paired flavor, as indicated by a reduced acceptance of the flavor. These effects are significantly different from acceptance of the drug-paired flavor in $B_{12}$-Ex4-treated animals (individual responses represented by white squares, overall group response represented in dark gray box). *, significantly different from vehicle (p<0.05); &, significantly different from all other groups (p<0.05). Key under (B) and (C) applies to both panels. Data in (A-C) are mean±SEM.

Figure 4:
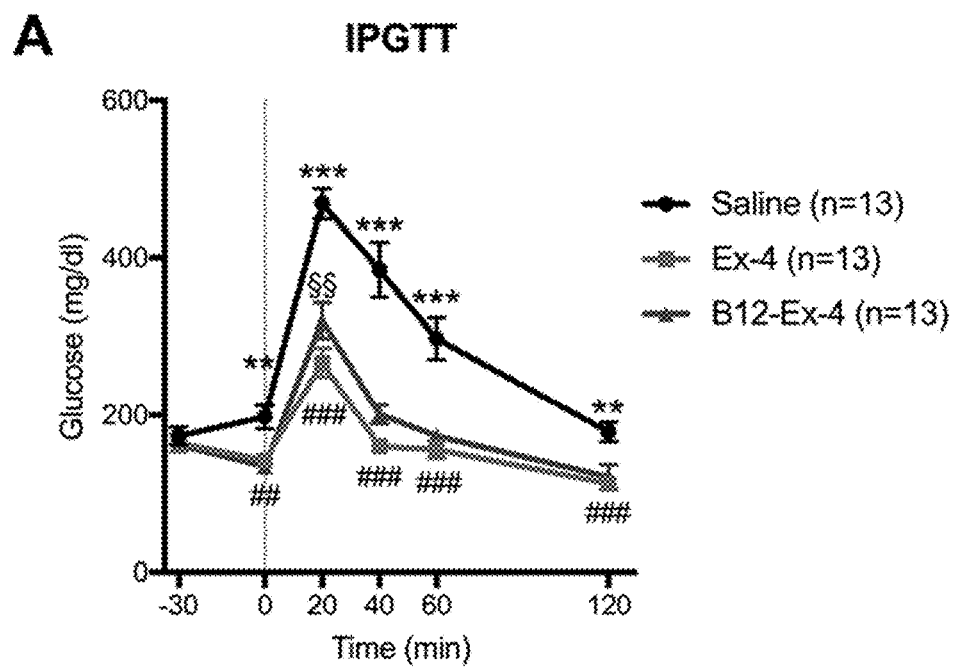
Figure 4:
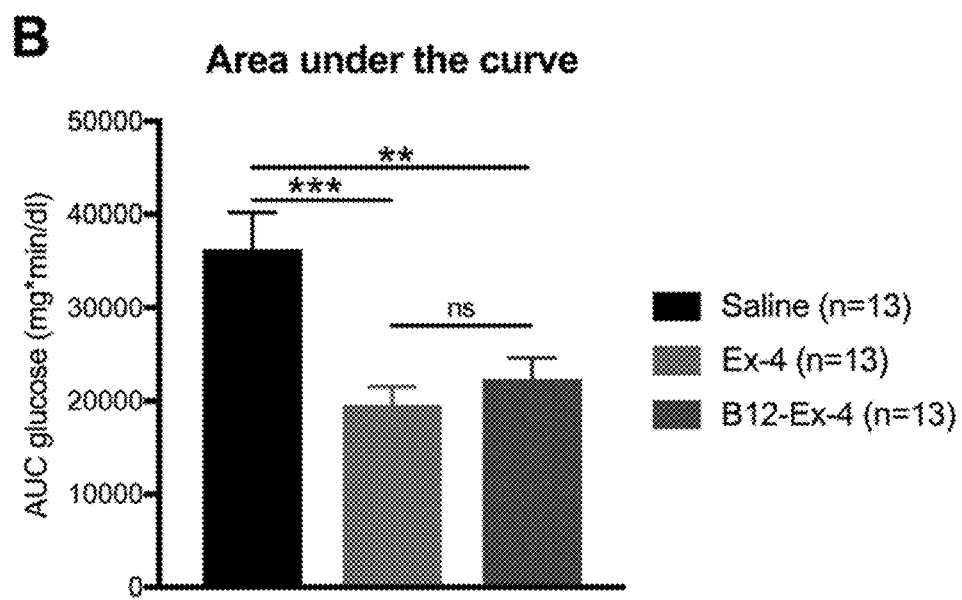

FIG. 4 is a series of graphs showing that systemic administration of $B_{12}$-Ex4 or Ex4 suppresses blood glucose in mice. In an intraperitoneal glucose tolerance test, Ex4 (5 μg/kg) and $B_{12}$-Ex4 (dose equimolar to Ex4) suppressed blood glucose levels prior to (t=0 min) and after (t=20, 40, 60, 120 min) IP glucose administration (A); vehicle versus $B_{12}$-Ex4:  p<0.01, * p<0.001; vehicle versus Ex4: $^{\#\#\#\#}$p<0.001; $B_{12}$-Ex4 versus Ex4: $^{\S\S}$ p<0.01. Area under the curve analyses from 0-120 min (i.e., post-glucose load) show that $B_{12}$-Ex4 (blue) and Ex4 (red) reduce AUC compared to saline vehicle (white) (B); * p<0.05, *** p<0.001. Data are mean±SEM.

Figure 5:
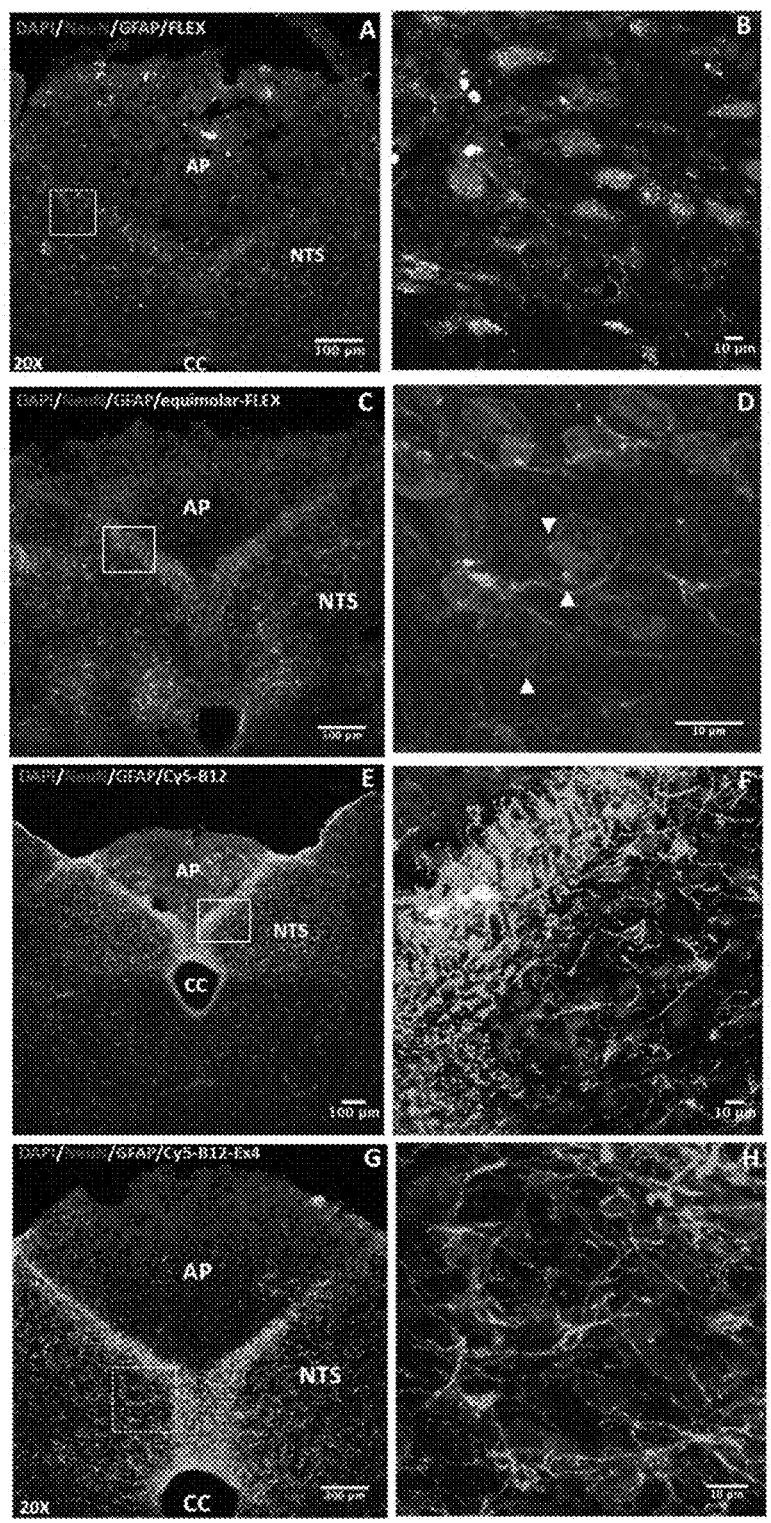

FIG. 5 is a series of graphs showing that systemically-delivered fluorescently labeled Ex-4 (Flex) highly penetrates within the DVC, whereas Cy5-$B_{12}$ and Cy5-$B_{12}$-Ex4 do not. Images were acquired at 10-20× (A,C,E,G) or 63× (with 2-3× optical zoom) (B,D,F,H) magnifications. Brains were processed for immunohistochemistry to label Flex, Equimolar-Flex, Cy5-$B_{12}$ and Cy5-$B_{12}$-Ex4 (yellow), astrocytes (GFAP; green) and neurons (NeuN; red). Sections were counterstained using DAPI (blue) to visualize cell nuclei. (B) Flex and (D) equimolar-Flex immunoreactivity is readily visualized in neurons and astrocytes in the DVC. (F) Cy5-$B_{12}$ and (H) Cy5-$B_{12}$-Ex4 are not present either in neurons or in astrocytes within the DVC. AP, area postrema; CC, central canal; DVC, dorsal vagal complex; NTS, nucleus tractus solitarius.

Figure 6:
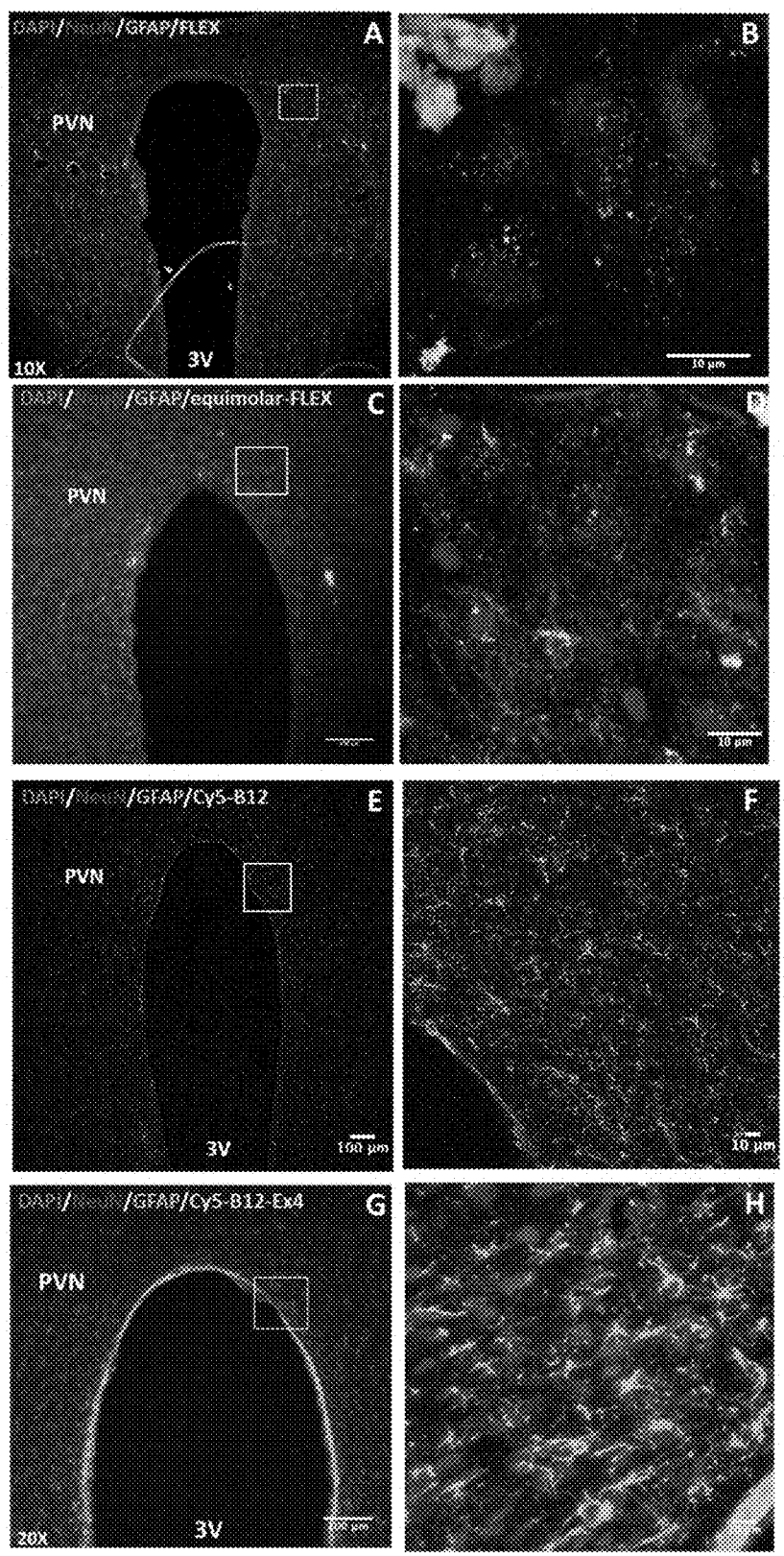

FIG. 6 is a series of graphs showing that systemically-delivered fluorescently labeled Ex-4 (Flex) highly penetrates within the PVN, whereas Cy5-$B_{12}$ and Cy5-$B_{12}$-Ex4 do not. Images were acquired at 10-20× (A,C,E,G) or 63× (with 2-3× optical zoom) (B,D,F,H) magnifications. Brains were processed for immunohistochemistry to label Flex, Equimolar-Flex, Cy5-$B_{12}$ and Cy5-$B_{12}$-Ex4 (yellow), astrocytes (GFAP; green) and neurons (NeuN; red). Sections were counterstained using DAPI (blue) to visualize cell nuclei. (B) Flex and (D) equimolar-Flex immunoreactivity is readily visualized in neurons in the PVN. (F) Cy5-$B_{12}$ and (H) Cy5-$B_{12}$-Ex4 are not present either in neurons or in astrocytes within the PVN. 3V, third ventricle; PVN paraventricular hypothalamic nucleus.

Figure 7:
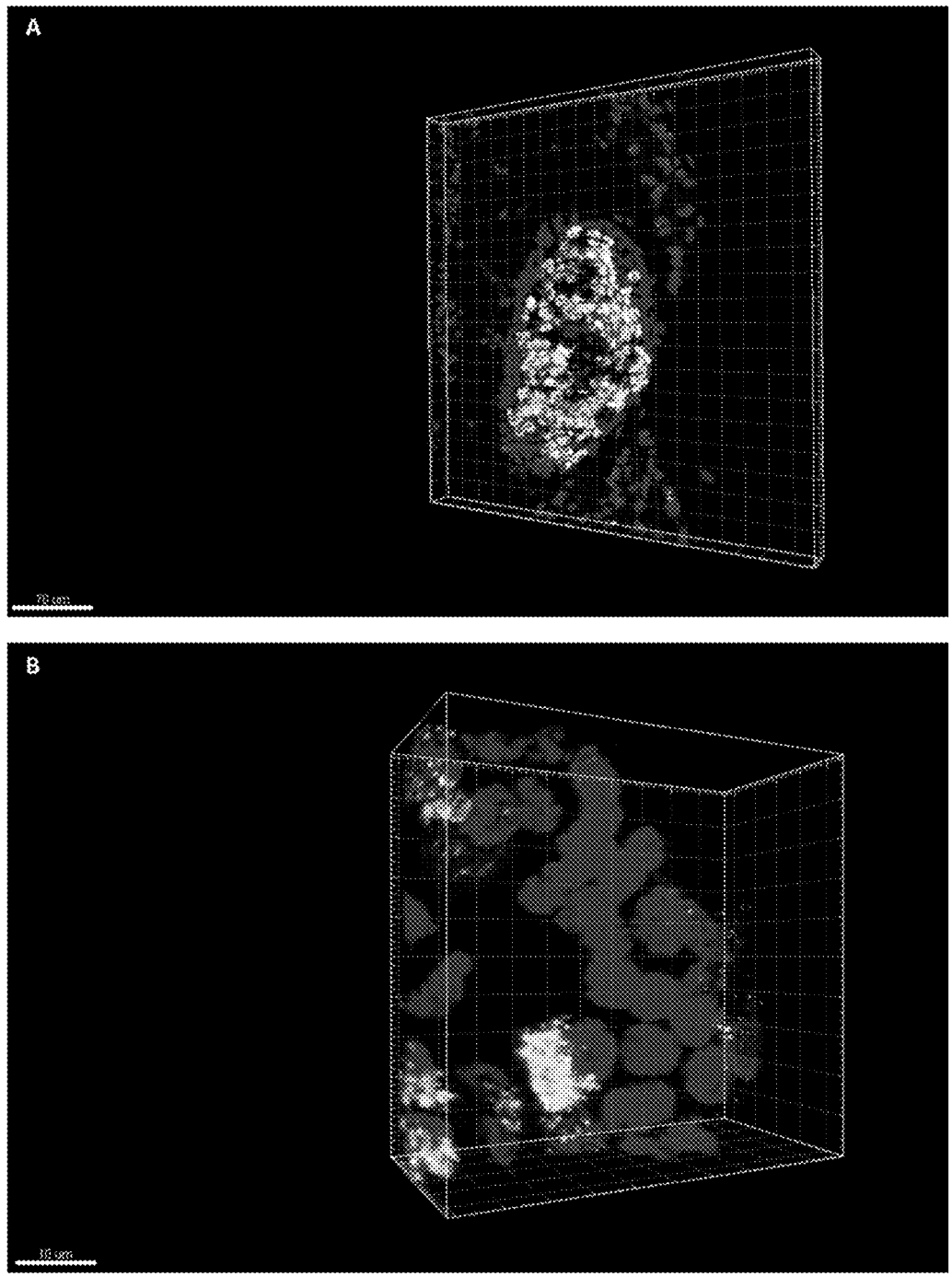

FIG. 7 is a series of graphs showing that systemically-delivered Cy5-$B_{12}$-Ex4 is colocalized with insulin in the pancreas. The representative still images from three-dimensional rotational videos (Supplemental Materials) demonstrate that Cy5-$B_{12}$-Ex4 (yellow) is colocalized with insulin (red) in pancreatic beta cells. Sections were counterstained with DAPI (blue). Videos and corresponding representative images were taken from a z-stack (2 μm step size) at 40× (A; Video 1) and from a z-stack (1 μm step size) at 40× with 4-5× optical zoom (B; Video 2).

Figure 8:
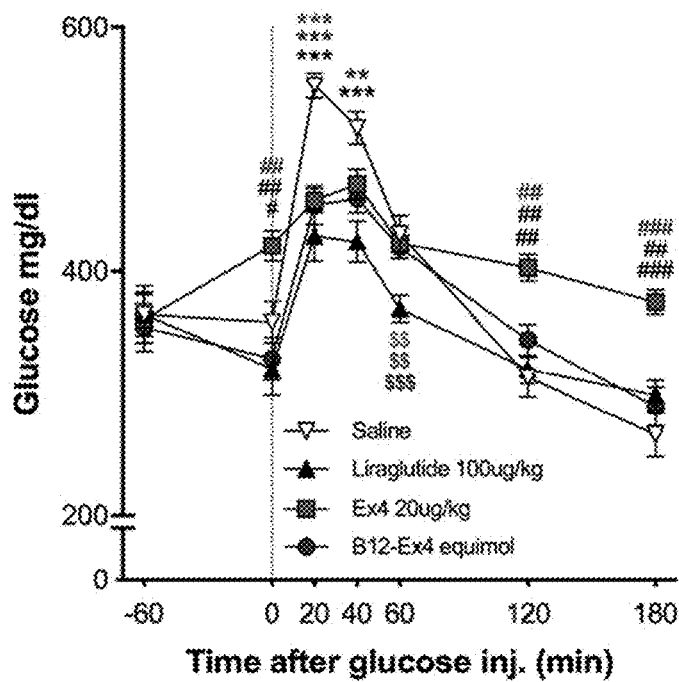
Figure 8:
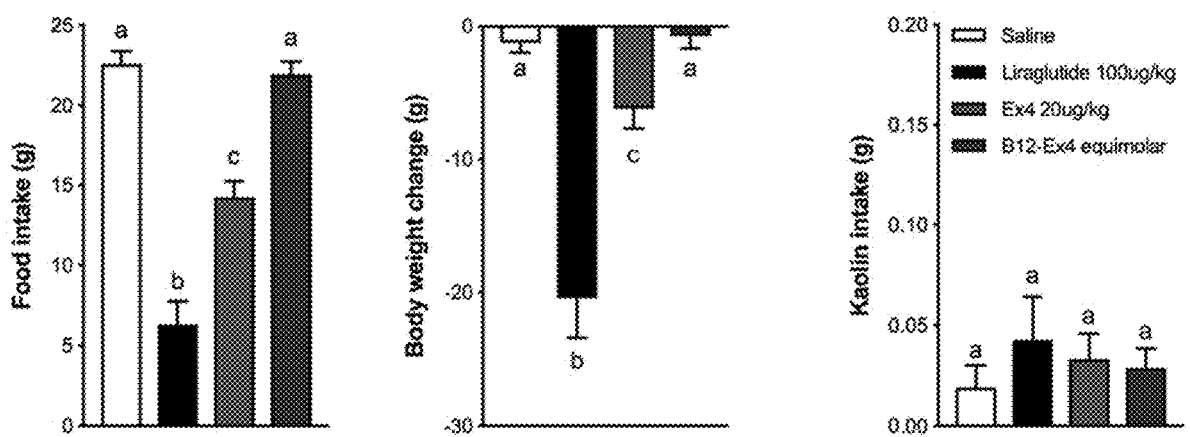

FIG. 8 is a series of graphs showing a standard oral glucose tolerance test performed in Goto-Kakazaki rats, a form of naturally diabetic lean rat, along with food intake and nausea measurements.

DETAILED DESCRIPTION OF THE INVENTION

Referring to the figures, wherein like numeral refer to like parts throughout, the present invention comprises the use of vitamin $B_{12}$ conjugation to a glucagon-like peptide-1 receptor (GLP-1R) agonist prior to administration to provide glycemic control in T2DM patients without eliciting unwanted hypophagia and nausea. It should be recognized that Vitamin $B_{12}$ analogs, including but not limited to, cobinamides may be employed for the present invention.

Recent work demonstrated that covalent conjugation of the GLP-1R agonist exendin-4 (Ex4) to vitamin $B_{12}$ (Cyanocobalamin; $B_{12}$) between the vitamin 5'-OH group and the K12 position of Ex4 retains picomolar agonism (68 pM) of the GLP-1R, either as the free conjugate ($B_{12}$-Ex4—used in this study; see also FIG. 1) or bound to Intrinsic Factor (IF; 126 pM), a $B_{12}$ transport protein critical for $B_{12}$ absorption in humans. This work also confirmed that IF bound $B_{12}$-Ex4 with low nanomolar affinity (as occurs with cyanocobalamin).

Interestingly, while Ex4 readily penetrates the CNS, little is known about the penetrance of $B_{12}$ in the brain. Uptake of $B_{12}$ into the brain is putatively a receptor-mediated process with megalin (a receptor capable of TCII-$B_{12}$ uptake in the kidney, for example) being expressed in the choroid plexus. Additional evidence points to the importance of the CD320 receptor, as genetic ablation in mice results in severe cobalamin deficiency in the mouse brain, as well as the transmembrane protein amnionless, natural mutations of which result in Imerslund-Gräsbeck syndrome and congenital cobalamin malabsorption. Collectively, this information points to a receptor-mediated process of $B_{12}$ blood-brain barrier penetrance, but little is known of where $B_{12}$ is transported in the brain, and to what extent, relative to total concentrations. It is evident that CNS uptake is considerably lower compared to other organs, especially the liver and kidney, with one recent study, using a $B_{12}$-$^{89}$Zr PET probe, revealing less than 0.1% injected dose per gram (ID/g) in brain in rat models with over 5% ID/g observed in pancreas. It was therefore hypothesized that a $B_{12}$-Ex4 conjugate would retain the incretin profile of a GLP-1R agonist to improve glucose tolerance, but prevent development of nausea/malaise through reduced, or redirected, CNS/hypothalamic penetration of the agonist.

The rat is a unique animal model for pre-clinical testing of the $B_{12}$-Ex4 conjugate. Rats, unlike humans and mice, demonstrate an unexpected hyperglycemic response to systemic Ex4 delivery. This hyperglycemic effect is unique to the Ex4 molecule (among approved GLP-1R agonists) in the rat and is due in part to CNS-mediated sympathetic activation. Further, rats show well-documented hypophagic effects to GLP-1R ligands mediated partly by accompanying acute effects on nausea/malaise, similar to humans, but not to mice. Rats were therefore used as the primary model to evaluate the effects of $B_{12}$-Ex4 on glycemic control, energy balance, and nausea/malaise, and these effects were compared with the response profile after peripheral administration of unconjugated Ex4. Given that Ex4 produces hypoglycemic effects in mice, similar to the effect observed in humans, blood glucose levels in mice were also assessed in a glucose tolerance test (GTT) upon $B_{12}$-Ex4 or Ex4 administration. The data presented here provide evidence for second-generation "cobalaminylated" GLP-1R agonists for the treatment of T2DM, with a pronounced profile of effects that include glucoregulation without anorexia or body weight loss, and most critically an absence of nausea/malaise

EXAMPLE

Materials and Methods

Animals.

Adult male Sprague Dawley rats (Charles River) were singly housed in hanging wire mesh cages. Four-month old C57BL/6J mice (Jackson Laboratory) were singly housed in plastic cages. All animals were housed under a 12 h:12 h light/dark cycle in a temperature- and humidity-controlled environment. Standard rodent chow (Purina 5001) and tap water were available ad libitum except where noted. Procedures were approved by the Institutional Care and Use Committee of the University of Pennsylvania.

Compounds.

$B_{12}$-conjugated exendin-4 ($B_{12}$-Ex4) was produced, characterized and screened for agonism at the GLP-1R ($EC_{50}$ of 68 pM, relative to 28 pM for Ex4 in the same assay), as previously described. One addition to the characterization was the measure of TCII binding of $B_{12}$-Ex4 (FIG. 1D), which was conducted at the Department of Clinical Medicine-Clinical Biochemistry, University of Aarhus, Denmark as described. $B_{12}$-Ex4, Ex4 (Bachem), and lithium chloride (LiCl; Sigma Aldrich) were dissolved in sterile 0.9% NaCl for peripheral injections. Injections were separated by at least 48 h. For most in vivo experiments, injections were administered using a within-subjects, Latin square design. The exception was the conditioned taste avoidance (CTA) study, which used a between-subjects design.

Effects of $B_{12}$-Ex4 on Energy Balance.

Shortly before the onset of the dark phase, rats (n=12) were given subcutaneous (SC) injection of $B_{12}$-Ex4 (1, 5, or 20 μg/kg) or vehicle (1 ml/kg sterile saline). Chow intake was measured at 1, 3, 6, and 24 h post-injection. Food spillage was accounted for in all intake measurements. Body weight was also measured at 0 and 24 h.

Effects of $B_{12}$-Ex4 on Glycemic Control During an Oral Glucose Tolerance Test (OGTT).

Rats (n=12) were deprived of food overnight before testing. On the morning of testing, just after the onset of the dark phase, water was also removed from the cage. A small drop of blood was collected from the tail tip and analyzed for blood glucose (BG) level using a standard glucometer (AccuCheck). Immediately after this baseline BG reading (t=−30 min), each rat received SC injection of $B_{12}$-Ex4 (5 or 20 μg/kg) or vehicle (1 ml/kg sterile saline); doses of drug were selected based on the results of the feeding study. Thirty minutes later (t=0 min), BG was measured and each rat received an oral gavage of glucose (2 g/kg). Subsequent BG readings were taken at 20, 40, 60, and 120 min after glucose gavage. After the final BG reading, food and water were returned.

Effects of Systemic Ex4 on Glycemic Control and Energy Balance.

The effects of unconjugated Ex4 were evaluated in an OGTT, using methods similar to those described above, with two major differences: SC injections were Ex4 (5 or 20 μg/kg) or vehicle (1 ml/kg sterile saline), and food intake and body weight change after the completion of the OGTT were monitored. Pre-weighed food was returned to the rats after the OGTT, and chow intake was measured for ~21.5 h (e.g., until 24 h after the SC injections). Spillage was accounted for in food intake measurements. Body weight was recorded at 0 and 24 h. For the OGTT, n=10 rats were tested; food and body weight data were collected from n=9 due to a technical error in food intake measurement.

Effects of $B_{12}$-Ex4 on Expression of a Conditioned Taste Avoidance (CTA).

Rats (n=8-10 per drug) were evaluated for expression of a CTA to a flavor paired with $B_{12}$-Ex4 (5 μg/kg, IP). Ex4 (5 μg/kg, IP) and LiCl (0.15M) were used as positive controls. A two-bottle test was used so each rat had access to a flavor that had been paired previously with vehicle (1 ml/kg saline, IP) and a flavor that had been paired previously with drug ($B_{12}$-Ex4, Ex4, or LiCl). See Supplemental Methods for more details.

Effect of $B_{12}$-Ex4 on Glycemic Control in Mice During an Intraperitoneal Glucose Tolerance Test (IPGTT).

The experimental procedure for IPGTT in mice was similar to that used for OGTT in rats. Briefly, mice (n=13; 8 females, 5 males) were food and water deprived for 4 h before and during the IPGTT. Testing was completed midlight phase. Blood was collected from the tail tip and analyzed for BG. Immediately after this baseline reading (t=−30 min), each mouse received IP injection of Ex4 (5 μg/kg), $B_{12}$-Ex4 (equimolar dose to Ex4), or saline (10 μl/g). Thirty minutes later (t=0 min), BG was measured and each mouse received an IP injection of glucose (2 g/kg). Subsequent BG readings were taken at 20, 40, 60, and 120 min after glucose injection. After the final BG reading, food and water were returned. Area under the curve (AUC) was calculated from 0-120 min (e.g., beginning at the time of glucose administration) using the trapezoidal method.

$B_{12}$-Exendin-4-Cyanine-5 (Cy5-$B_{12}$-Ex4) Synthesis.

$B_{12}$-Ex4 was synthesized as previously described. $B_{12}$-Ex4 (0.5 mg, 0.0001 mmol) was dissolved in PBS buffer pH 7.6 (450 μL) and sulfo-cyanine 5-NHS-ester (1 mg, 0.001 mmol) (Lumiprobe) was added (in 50 μL DMSO). The resulting solution was allowed to mix for 2 h at room temperature, protected from light, and then purified through RP-HPLC on a Shimadzu Prominence HPLC using a C18 column (Eclipse XDB-C18 5 μm, 4.6×150 mm). Solvents: A: 0.1% TFA water and B: Acetonitrile. Method: B %: 1-70% over 15 min. $t_R$: 12.1 min. Yield: 98%. Emission and excitation were 648 and 670 nm, respectively using a Varian Cary UV Spectrophotometer and Agilent Cary Eclipse Fluorescence Spectrophotometer, solvent $H_2O$/MeCN. LC-MS analysis (Shimadzu LCMS-8040, Method: 0.1% formic acid and 35% methanol water at 0.2 mL/min, DL temp: 150° C., heat block temp: 400° C.): expected m/z: 6923 [$B_{12}$-Ex4-$(Cy5)_2$], observed: 1383 $[M+5H]^{+5}$, 1728 $[M+4H]^{+4}$. See FIG. 1 for more information.

$B_{12}$-Cyanine-5 (Cy5-$B_{12}$) Synthesis.

Cy5-$B_{12}$ was synthesized through Huisgen/Sharpless 'Click' Chemistry. Cu(I) (1 mg, 0.005 mmol) and Tris[(1-benzyl-1H-1,2,3-triazol-4-yl)methyl]amine (3.5 mg, 0.006 mmol) were dissolved in 0.5 mL DMF/H2O (4:1 v/v). Once color change occurred, the previously synthesized $B_{12}$-Azide (3 mg, 0.002 mmol) and Cyanine-5 alkyne (0.5 mg, 0.0007 mmol) (Lumiprobe) was dissolved in the solution and allowed to stir at room temperature overnight protected from light. This was purified through RP-HPLC on a Shimadzu Prominence HPLC using a C18 column (Eclipse XDB-C18 5 μm, 4.6×150 mm). Solvents: A: 0.1% TFA water and B: Acetonitrile. Method: B %: 20-72% over 18 min. $t_R$: 4.7 min. Yield: 94%. LC-MS analysis (Shimadzu LCMS-8040, Method: 0.1% Formic acid and 35% methanol water at 0.2 mL/min, DL temp: 150° C., heat block temp: 400° C.): expected m/z: 2059 observed: 1031 $[M+2H]^{+2}$, 1042 $[M+Na+2H]^{+2}$, and 1050 $[M+K+2H]^{+2}$. Emission and excitation were 645 and 682 nm, respectively using a Varian Cary UV Spectrophotometer and Agilent Cary Eclipse Fluorescence Spectrophotometer, solvent $H_2O$. See FIG. 1 for more information.

GLP-1 Assay for Cy5-$B_{12}$-Ex4.

Agonism at the GLP-1 receptor was monitored using HEK-293 cells stably transfected with the GLP-1 receptor cultured in DMEM with 10% FBS, 1% pen/strep, and 250 μg/mL geneticin/g-418. Cells were plated on a rat-tail-collagen-coated 96-well plate at 60,000 cell/well and allowed to adhere overnight. The cells were infected with an adenovirus to express the H188 FRET reporter using a 25 MOI for 16-20 h in 75 μL of DMEM-1% FBS. After viral incubation, the cells were placed in 200 μL standard extracellular matrix with glucose and 0.1% BSA. Conjugates were added to each well at 5× the required concentration. Agonism was determined through an increase in 485/553 nm FRET ratio indicative of an increase in cAMP level through cAMP binding to an EPAC (exchange protein directly activated by cAMP).

Immunohistochemical Procedures and Confocal Imaging.

Rats (n=4/group) were given IP injection of fluorophore-labeled Ex-4 (Flex; 5 μg/kg; 0.0001 nM; AnaSpec), Cy5-$B_{12}$-Ex4 (5 μg/kg; 0.03 nM), Cy5-$B_{12}$ (5 μg/kg), or Cy5-$B_{12}$-Ex4 delivered at an equimolar dose to Flex (0.0001 nM). Rats were transcardially perfused 3 h after injection, using 0.1M PBS followed by 4% paraformaldehyde (PFA). Brains were collected and sections from the area postrema and hypothalamus were processed via immunohistochemistry for NeuN and GFAP, mounted, and coverslipped with DAPI mounting medium. Sections were visualized via confocal microscopy.

To evaluate the penetrance of $B_{12}$-Ex4 in the pancreas, rats (n=2) were given IP injection of Cy5-$B_{12}$-Ex4 (5 μg/kg) and transcardially perfused 3 h later with 4% paraformaldehyde in PBS. Pancreases were collected and sagittally sectioned, processed via immunohistochemistry for insulin, and coverslipped with DAPI mounting medium. Sections were visualized with confocal microscopy and three-dimensional rotational animations were rendered from the collected z-stack images using Imaris 8.1.2 (Bitplane).

Statistical Analyses.

See Supplemental Methods.

Results $B_{12}$-Ex4 has Potent Beneficial Effects on Glycemic Control, but Minimal Impact on Feeding and Body Weight in Rats.

Ex4 and other GLP-1R agonists reduce blood glucose levels, and are used clinically to treat T2DM. In addition, the food intake- and body weight-suppressive effects of GLP-1R agonists have highlighted the utility of these pharmacotherapies for the treatment of obesity. To evaluate whether the metabolic effects of $B_{12}$-Ex4 are similar to those of other GLP-1R agonists such as unconjugated Ex4, the effects of SC injection of $B_{12}$-Ex4 on energy balance and glycemic control were evaluated. To confirm TCII binding of $B_{12}$ in its Ex4 conjugated form (i.e. $B_{12}$-Ex4), a radio chase assay using $^{57}$Co-labelled $B_{12}$ was conducted and confirmed low nanomolar binding (~75 nM) was maintained (FIG. 1D).

First, to test whether $B_{12}$-Ex4 has similar intake- and body weight-suppressive effects as Ex4, rats were given SC injection of $B_{12}$-Ex4 (0, 1, 5, or 20 μg/kg in 1 ml/kg sterile saline), and subsequent food intake (1, 3, 6, 24 h) and body weight gain were measured. The highest dose of $B_{12}$-Ex4, 20 μg/kg, significantly suppressed food intake at 3 h and 6 h post-injection (FIG. 2A; drug×time interaction, $F_{9,99}$=3.69, p<0.001; 0 μg/kg versus 20 μg/kg, p<0.05 at 3 h and 6 h). No other significant effects on food intake were observed at other times or by other doses of drug (all other p>0.05). There was also no significant effect of $B_{12}$-Ex4 on 24 h body weight change (FIG. 2B; $F_{3,33}$=0.50, p=0.69), which is consistent with the fact that cumulative 24 h energy intake was similar among the treatment conditions.

Next, the glycemic effects of $B_{12}$-Ex4 (5 or 20 μg/kg) or vehicle (1 ml/kg sterile saline, SC) were evaluated via OGTT. $B_{12}$-Ex4 significantly reduced blood glucose levels in the OGTT (FIG. 2C; main effect of drug, $F_{2,22}$=4.01, p<0.04; drug×time interaction, $F_{10,110}$=17.29, p<0.000001). Posthoc analyses showed that both doses of $B_{12}$-Ex4 significantly suppressed BG at 20 and 40 min after glucose gavage (versus vehicle, all p<0.05). A dose-responsive effect is also suggested by the finding that 20 μg/kg $B_{12}$-Ex4 had more potent BG-suppressive effects than 5 μg/kg at 20 min after glucose gavage (p<0.05). Interestingly, BG levels were increased by both doses of $B_{12}$-Ex4 at 60 min and by the higher dose at 120 min (all p<0.05). Importantly, injection of $B_{12}$-Ex4 had no effect on blood glucose levels on its own (t=0, all p>0.05).

Systemic Injection of Ex4 Produces Hyperglycemia, Hypophagia, and Weight Loss.

The rat is a particularly interesting model to test the effects of an Ex4-based drug on glycemic and energy balance control, because rats exhibit a hyperglycemic response to acute peripheral administration of Ex4 due to sympathetic activation, but also show pronounced reductions in feeding and body weight gain. To evaluate the effects of SC administration of unconjugated Ex4 on these measures, and to be able to more directly compare the effects of $B_{12}$-Ex4 to those of Ex4, an OGTT was administered to rats after SC injection of Ex4 (5 or 20 μg/kg) or vehicle (1 ml/kg), and subsequent chow intake and body weight were monitored after the OGTT. Similar to previous findings, systemic Ex4 produced a pronounced hyperglycemic response in the rats (FIG. 3A, main effect of drug, $F_{2,18}$=8.84, p<0.01; drug×time interaction, $F_{10,90}$=11.89, p<0.000001). Injection of either dose of Ex4 increased BG on its own (e.g., before administration of glucose; at t=0 min, vehicle versus 5 or 20 µg/kg, p<0.05). BG levels remained significantly elevated in Ex4-treated rats at 40, 60, and 120 min after the glucose gavage (vehicle versus 5 or 20 µg/kg, all p<0.05).

When food was returned after the last BG reading, Ex4-treated rats ate significantly less than did vehicle-treated controls in the subsequent 21.5 h (FIG. 3B, $F_{2,16}$=43.74, p<0.000001; vehicle versus 5 or 20 µg/kg, p<0.05) and gained less body weight (FIG. 3C, $F_{2,16}$=8.31, p<0.01; vehicle versus 20 µg/kg, p<0.05). These results demonstrate the unique constellation of effects produced by peripheral Ex4 administration in the rat, and more importantly, highlight the distinct differences between Ex4 and $B_{12}$-Ex4 for glycemic and energy balance control.

Ex4 Elicits Expression of a Robust CTA that is not Observed with $B_{12}$-Ex4.

GLP-1R agonists such as Ex4 have undesired side effects including nausea/malaise. To evaluate whether $B_{12}$-Ex4 produces nausea/malaise, rats were evaluated for expression of a conditioned taste avoidance (CTA) to $B_{12}$-Ex4 (5 µg/kg, IP). Additional groups of rats were evaluated in this experiment for CTA to Ex4 (5 µg/kg, IP) or to LiCl (0.15M, IP), which is well known to produce nausea and CTA in rodents. As shown in FIG. 3D, acceptance of the drug-paired flavor was significantly higher in the $B_{12}$-Ex4-treated group compared to either LiCl or Ex4 ($F_{2,24}$=5.29, p<0.01; $B_{12}$-Ex4 versus LiCl or Ex4, p<0.05; LiCl versus Ex4, p>0.05), suggesting that $B_{12}$-Ex4 does not produce the same nausea/malaise as Ex4.

In Mice, $B_{12}$-Ex4 and Ex4 Suppress Blood Glucose Levels in a Glucose Tolerance Test.

To confirm the ability of $B_{12}$-Ex4 to improve glycemic control in species that do not exhibit Ex4-induced stress-mediated hyperglycemic responses, the glycemic effects of equimolar doses of $B_{12}$-Ex4 and Ex4 were tested via IPGTT in mice. In contrast to rats, and more in line with human data, Ex4 administration strongly attenuated the increase in blood glucose levels after IP glucose administration. Similarly, $B_{12}$-Ex4 reduced blood glucose levels in the IPGTT (FIG. 4A; main effect of drug, $F_{2,24}$=67.13, p<0.0001; drug×time interaction, $F_{10,120}$=15.07, p<0.0001). Posthoc analyses showed that both compounds significantly suppressed BG at 20, 40, 60, and 120 min after glucose injection (all p<0.05). Interestingly, injection of $B_{12}$-Ex4 or Ex4 also reduced BG levels prior to IP glucose injection (t=0, all p<0.05). Although Ex4 had a more potent effect on BG at 20 min compared to $B_{12}$-Ex4 (p<0.05), area under the curve analyses revealed that both compounds had hypoglycemic effects post-glucose load compared to saline (FIG. 4B; $F_{2,24}$=62.74, p<0.0001; vehicle versus $B_{12}$-Ex4 or versus Ex4, p<0.05).

Unlike Ex4, $B_{12}$-Ex4 does not Readily Penetrate into the CNS.

Previous work shows that Ex4 crosses the blood-brain barrier to exert effects on energy balance and illness/malaise. As $B_{12}$-Ex4 treatment produces the glycemic benefits associated with Ex4 without producing the centrally-mediated effects of hypophagia and nausea, this suggests that $B_{12}$-Ex4 may be excluded from the CNS. To evaluate this possibility, rats were treated systemically with a fluorescent-tagged version of $B_{12}$-Ex4 (Cy5-$B_{12}$-Ex4), and penetrance into the brain was evaluated using confocal microscopy. The results were compared with CNS penetrance of a fluorescent-tagged version of Ex4 (Flex), which has been shown to penetrate into the CNS, and fluorescent-tagged $B_{12}$ (Cy5-$B_{12}$). The presence of each of these fluorescent compounds was evaluated in the dorsal vagal complex (DVC; FIG. 5) and paraventricular nucleus of the hypothalamus (PVN; FIG. 6), due to the known importance of these areas in mediating the feeding effects of GLP-1R activation and the hyperglycemic response observed in rats after systemic Ex4. Consistent with previous data, Flex was observed in the DVC, and also was observed within the PVN. In contrast, Cy5-$B_{12}$ and Cy5-$B_{12}$-Ex4 were not detected in either nucleus, suggesting that exogenously-injected $B_{12}$ does not readily penetrate into these regions of the CNS, and hence that conjugation of $B_{12}$ to Ex4 greatly reduces or prevents Ex4 from entering the same areas.

$B_{12}$-Ex4 is Colocalized on Insulin Producing Pancreatic Beta Cells.

The finding that peripherally administered $B_{12}$-Ex4 is not detected in the DVC or PVN suggests that the glycemic effects of the compound are likely mediated via peripheral actions. The pancreas is a prime candidate for a peripheral site of action responsible for the glycemic-suppressive effects of $B_{12}$-Ex4. Indeed, GLP-1R agonists can act directly on pancreatic beta cells to stimulate insulin release, thereby improving blood glucose levels. To assess whether $B_{12}$-Ex4 is taken up by insulin-producing pancreatic beta cells, rats were given systemic injection of Cy5-$B_{12}$-Ex4 (5 µg/kg) and colocalization with insulin-expressing cells was analyzed in the pancreas with 3-dimensional confocal microscopy. Results show robust colocalization of Cy5-$B_{12}$-Ex4 with insulin in pancreatic sections (FIG. 7; Supplemental Materials, Videos 1 and 2), supporting the hypothesis that $B_{12}$-Ex4 acts at the pancreas to improve glycemic control.

Discussion

GLP-1-based pharmacotherapies for T2DM have been revolutionary in providing largely safe and efficacious means to reduce chronic hyperglycemia. However, due to side effects of current GLP-1-based compounds including anorexia, nausea, and vomiting, nearly one in four T2DM patients are not able to benefit from the full pharmaceutical advantages of these pharmacotherapies. There is clearly a critical need to develop a new generation of GLP-1 pharmacotherapies that provide hypoglycemic benefit without eliciting detrimental side effects. Although the hypophagic effects of GLP-1R agonists are often attractive to clinicians and to T2DM patients with overweight or obesity, much of the same CNS circuitry underlying GLP-1R ligand-mediated anorexia is also partially responsible for mediating nausea/malaise. Moreover, weight loss may be undesirable for some T2DM patients, such as individuals with a normal BMI. As the hypophagia and illness-like effects of existing GLP-1R agonists require CNS penetrance and direct central action, it was intended to create a GLP-1R agonist conjugate that minimizes anorexia and nausea by reducing CNS penetrance, but that retains potent pharmacodynamics and pharmacokinetic profile on peripheral GLP-1R populations to exert glycemic benefits. This report shows for the first time the ability of $B_{12}$-Ex4 to improve glucose tolerance in rodents without producing hypophagia, body weight loss, or CTA. Supporting a recent finding showing that vitamin $B_{12}$ is not actively transported into the adult brain, current immunohistochemical data suggest that the unique profile of glycemic effects without the same hypophagic/CTA-producing effects of Ex4 involves a direct effect of $B_{12}$-Ex4 on pancreatic beta cells coupled with a virtual absence of CNS penetrance of the compound.

The rat provides a unique model for the proof-of-concept testing needed for the preclinical evaluation of $B_{12}$-Ex4. Rats show an unexpected hyperglycemic response to Ex4, due in part to a CNS-mediated activation of the sympathetic nervous system. In addition, like humans, rats show a pronounced profile of behavioral effects to systemic Ex4 including reduced food intake and body weight, as well as illness-like behaviors, again due to CNS action. $B_{12}$-Ex4 did not produce the same suppression of food intake, reduction in body weight, and induction of CTA as did Ex4 in rats. The effect of $B_{12}$-Ex4 on glycemic control was also evaluated in mice, a species in which Ex4 produces a hypoglycemic response similar to that observed in humans. In mice, $B_{12}$-Ex4 and unconjugated Ex4 each elicited hypoglycemic responses in an IPGTT. Collectively, these data provide an ideal preclinical set of outcomes to support the therapeutic potential of this conjugate as a future antidiabetic drug for humans.

The in vivo behavioral data were supported by our immunohistochemical analyses showing a virtual absence of $B_{12}$-Ex4 CNS penetrance in the DVC and PVN, two areas of the brain showing unconjugated Ex4 penetrance and believed to mediate in part the hyperglycemic, hypophagic, body weight suppressive, and malaise-producing effects of Ex4 in rats. Future studies are warranted to identify the mechanisms responsible for the minimal CNS uptake of $B_{12}$ and the molecular mechanisms by which $B_{12}$ conjugation reduces CNS Ex4 access. It will also be important to address whether higher doses of $B_{12}$-Ex4 are able to more effectively penetrate the CNS. The 5 µg/kg dose of Cy5-$B_{12}$-Ex4 used for this study was selected because 5 µg/kg $B_{12}$-Ex4 had no effect on feeding or body weight in rats, but produced hypoglycemia in the OGTT, suggesting that a lower dose of $B_{12}$-Ex4 elicits an optimal profile of glycemic and energy balance effects. In contrast, a higher dose of $B_{12}$-Ex4 (20 µg/kg) reduced blood glucose but also caused a small but significant transient suppression of feeding, suggesting that higher doses may have a slightly different pattern of effects. Nevertheless, these results clearly underscore the reduced CNS penetrance but retention of glycemic benefits by lower doses of $B_{12}$-Ex4.

As $B_{12}$-Ex4 is not extensively penetrating into the CNS, pancreatic GLP-1R represents the likely cellular substrate mediating the hypoglycemic effects of $B_{12}$-Ex4. Further analyses supported this hypothesis, as immunohistochemical data showed colocalization of Cy5-$B_{12}$-Ex4 with insulin in the pancreas. This suggests that $B_{12}$-Ex4 may exert its glycemic effects via direct action at pancreatic beta cells, while CNS-mediated effects of GLP-1R activation such as hypophagia, nausea, and malaise are minimal or absent due to lack of penetrance of $B_{12}$-Ex4 into the brain, consistent with previously reported radio-probe data.

The current data provide novel mechanistic evidence that $B_{12}$ conjugation to a GLP-1R agonist can be used as a means to retain the hypoglycemic properties of GLP-1R agonists but greatly reduce the CNS-mediated anorexia and illness effects observed with all current approved GLP-1-based ligands. These studies are far from the complete set of in vivo glycemic analyses needed for $B_{12}$-Ex4, but certainly justify the need for more comprehensive future analyses. Further investigations are warranted to examine the acute actions of $B_{12}$-Ex4 in diabetic animal models, as well as to evaluate the metabolic effects of chronic $B_{12}$-Ex4 administration. It will also be critical to evaluate whether, and to what extent, $B_{12}$-Ex4 may localize within other CNS nuclei not examined here. Collectively, these data highlight the discovery that $B_{12}$ conjugation to Ex4 results in a next-generation incretin therapeutic with the clinically desired hypoglycemic effects but not concomitant hypophagia, body weight loss and, most notably, illness-like behaviors, ideal for the future of T2DM treatment in humans. This method of conjugation may also be broadly beneficial to other therapeutics that would benefit from reduced CNS penetrance.

Example 2

Referring to FIG. 8, Testing of Ex-4 at 20 ug/Kg, $B_{12}$-Ex4 at equimolar to Ex-4, and liraglutide at 100 ug/Kg were screened for glucoregulation, food intake reduction and nausea (kaolin consumption). All drugs were administered at 60 minutes pre-glucose bolus, food intake and nausea were tracked over 6 hours. The results demonstrate that, unlike normal Ex4, $B_{12}$-Ex4 does not cause hyperglycemia (which Ex4 does do in rats and liraglutide does not). $B_{12}$-Ex4 infant behaves like liraglutide and controls glucose levels. Unlike liraglutide, we see significantly reduced body weight loss.

What is claimed is:

1. A method of mitigating the side effects of administration of a glucagon-like peptide-1 receptor agonist to a subject, comprising the steps of:
    conjugating the agonist to a cobalamin to form a conjugated complex prior to administration; and
    administering the conjugated complex to the subject, wherein the agonist is exendin-4.

2. The method of claim 1, wherein the conjugated complex is characterized by increased resistance to dipeptidyl peptidase (DPP-IV) degradation as compared to the agonist without conjugation to the cobalamin.

3. The method of claim 1, wherein the conjugated complex is characterized by a reduced ability to penetrate into the central nervous system of the subject as compared to the agonist without conjugation to the cobalamin.

4. The method of claim 1, wherein the conjugated complex is characterized by glycemic control in the subject that is similar to glycemic control of the agonist without conjugation to the cobalamin.

5. The method of claim 1, wherein the cobalamin is vitamin $B_{12}$.

6. The method of claim 1, wherein the side effects include anorexia.

7. The method of claim 1, wherein the side effects include malaise.

8. The method of claim 1, wherein the side effects include hypophagia.

9. The method of claim 1, wherein the side effects include nausea.

* * * * *